(12) United States Patent
Cadogan et al.

(10) Patent No.: US 6,837,610 B2
(45) Date of Patent: Jan. 4, 2005

(54) BIOPROCESS CONTAINER, BIOPROCESS CONTAINER MIXING DEVICE AND METHOD OF USE THEREOF

(75) Inventors: David Phillip Cadogan, Middletown, DE (US); Scott Lester Davidson, Seaford, DE (US); Thomas Joseph Edwards, Seaford, DE (US); John Kun Hung Lin, Middletown, DE (US); Steven Michael Lloyd, Symrna, DE (US); Tony Ray McKee, Dover, DE (US)

(73) Assignee: ILC Dover LPP, Frederica, DE (US)

( * ) Notice: Subject to any disclaimer, the term of this patent is extended or adjusted under 35 U.S.C. 154(b) by 76 days.

(21) Appl. No.: 10/256,070

(22) Filed: Sep. 27, 2002

(65) Prior Publication Data

US 2004/0062140 A1 Apr. 1, 2004

(51) Int. Cl.⁷ .................................. B01F 11/00
(52) U.S. Cl. ..................... 366/144; 366/149; 366/275
(58) Field of Search ................. 366/144, 149, 366/275; 435/289.1, 302.1; 604/114, 409

(56) References Cited

U.S. PATENT DOCUMENTS

| | | | | |
|---|---|---|---|---|
| 2,124,983 A | * | 7/1938 | Martin | 366/275 |
| 2,662,520 A | * | 12/1953 | McMahon | 435/1.3 |
| 2,845,929 A | * | 8/1958 | Strumia | 604/113 |
| 3,306,829 A | | 2/1967 | Patterson et al. | |
| 3,518,393 A | * | 6/1970 | Barclay et al. | 219/772 |
| 3,647,397 A | | 3/1972 | Coleman | |
| 3,656,716 A | * | 4/1972 | Ljungerg et al. | 366/275 |
| 4,114,522 A | | 9/1978 | Nagamine | |
| 4,177,575 A | | 12/1979 | Brooks | |
| 4,207,007 A | * | 6/1980 | Yamschikov et al. | 366/275 |
| 4,231,425 A | * | 11/1980 | Engstrom | 165/156 |
| 4,242,001 A | | 12/1980 | Meintker et al. | |
| 4,801,777 A | * | 1/1989 | Auerbach | 604/114 |
| 4,808,159 A | * | 2/1989 | Wilson | 604/6.13 |
| 5,114,045 A | * | 5/1992 | Herpe | 222/105 |
| 5,312,754 A | * | 5/1994 | Bryan-Brown | 366/275 |
| 5,456,586 A | * | 10/1995 | Carson | 366/275 |
| 5,533,804 A | | 7/1996 | Larsson et al. | |
| 5,555,796 A | | 9/1996 | Kortschot et al. | |
| 5,795,330 A | | 8/1998 | Tofighi et al. | |
| 5,941,635 A | | 8/1999 | Stewart | |
| 6,029,563 A | | 2/2000 | Nakagawa et al. | |
| 6,076,457 A | | 6/2000 | Vallot | |
| 6,089,143 A | | 7/2000 | Figueroa | |
| 6,190,913 B1 | | 2/2001 | Singh | |
| 6,213,007 B1 | | 4/2001 | Lande | |
| 6,279,463 B1 | | 8/2001 | Kajiwara | |
| 6,364,520 B1 | | 4/2002 | Steele | |
| 6,416,215 B1 | | 7/2002 | Terentiev | |
| 6,453,683 B1 | * | 9/2002 | Wisniewski et al. | 62/75 |
| 6,634,783 B2 | * | 10/2003 | Baron | 366/204 |

OTHER PUBLICATIONS

U.S. Appl. No. 2002/0162650, published Nov. 7, 2002 to MacKelvic.
U.S. Appl. No. 2002/0105856, published Aug. 8, 2002, to Terentiev.
International Search Report dated Sep. 10, 2004, PCT/US03/23368.

* cited by examiner

Primary Examiner—Tony G. Soohoo
(74) Attorney, Agent, or Firm—Stevens, Davis, Miller & Mosher, L.L.P.

(57) ABSTRACT

A bioprocess container consists of a flexible container, placed inside a heat exchanger. By providing a disposable agitation device inside the sealed container, a filled container can be stirred without having to open the container. Possible agitation elements include traditional stirrers, rotating magnetic rods, bladder devices integral with the structure of the container, as well as different devices for manipulating the shape of the sealed container. Finally, a containment disk is used to ensure that the magnetic rod is maintained in the magnetic field.

6 Claims, 3 Drawing Sheets

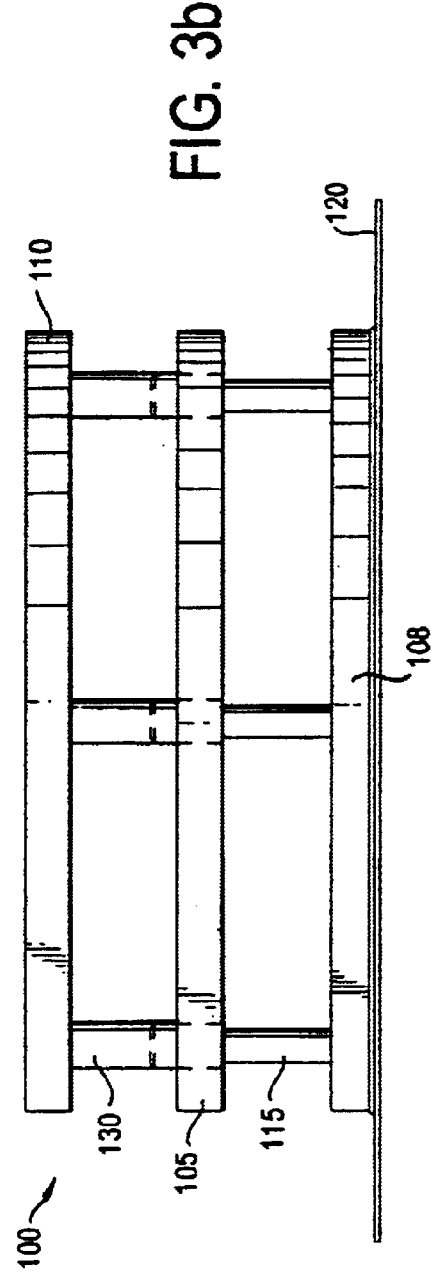
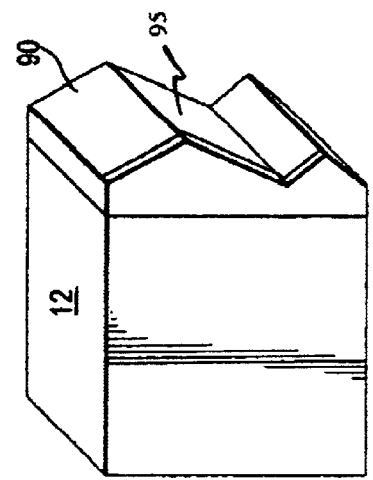
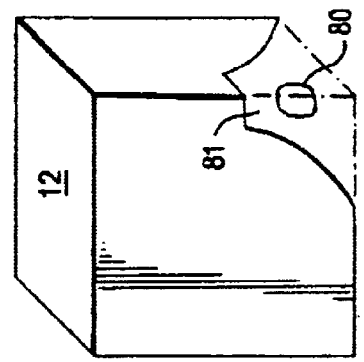
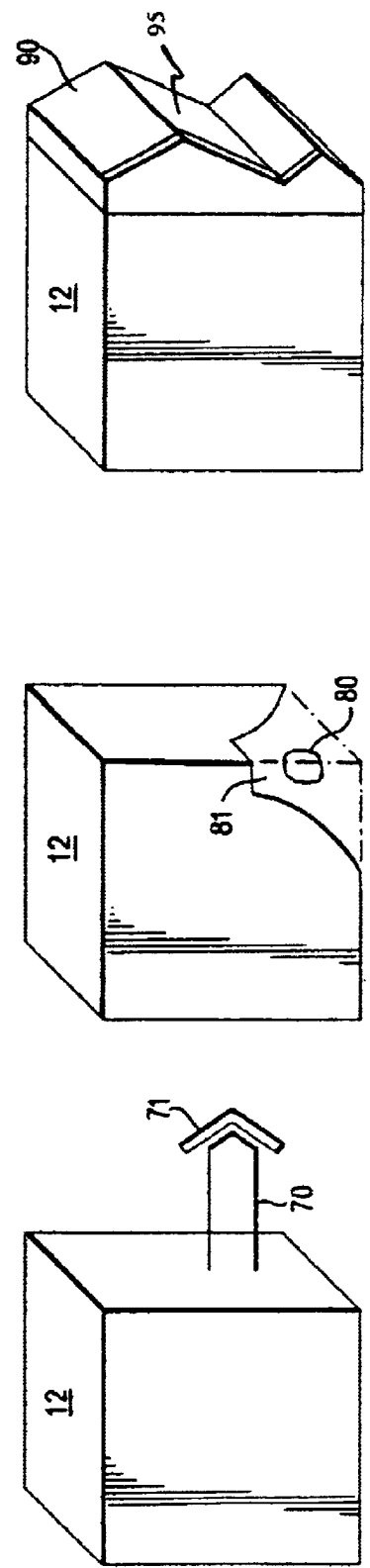

US 6,837,610 B2

BIOPROCESS CONTAINER, BIOPROCESS CONTAINER MIXING DEVICE AND METHOD OF USE THEREOF

BACKGROUND OF THE INVENTION

1. Field of the Invention

The present invention relates to the field of mixing containers of fluids, most often at least one liquid. More specifically, the device and method of the invention concern disposable, sealed containers and various devices and processes for mixing the contents therein.

2. Description of the Related Art

The biopharmaceutical process industry has been moving toward technologies that use disposable manufacturing components versus stainless steel tanks and piping. One key component is bioprocessing containers (BPCs). Conventional manufacturing, mixing and/or stirring devices have been used in this type of industry for a considerable period of time. In one type of system, the various ingredients or components are introduced into a typical glass beaker.

When a large scale production is required, the glass beaker may be replaced by a large metal vat or other conventional industrial vessel that also provides heating and cooling capacity. In either system, the components are sequentially or consecutively added to the vessel where the mixing and/or stirring is conducted. In such systems, a stirring device is generally inserted through the upper, open face of the container and powered from an external source. Additionally, reuse of the conventional system requires significant cleaning and sterilization processes to ensure the absence of undesirable materials.

Improvements to the traditional beaker or industrial vat mixing systems include those described in U.S. Pat. No. 5,795,330, No. 5,941,635, No. 6,076,457, and No. 6,190,913, each of which is herein incorporated by reference in its entirety.

SUMMARY OF THE INVENTION

In order to overcome the problems associated with conventional BPC mixing devices, the present invention utilizes a new container-heat exchanger combination. Specifically, the BPC of the invention generally includes a flexible container, placed inside a rigid heat exchanger. In one embodiment, the flexible container is destroyed and replaced after use to eliminate the necessity of cleaning and sterilization. The shape of the heat exchanger is selected to correspond to the shape of the flexible container when the container is filled. Because the container is inserted into a cavity in the heat exchanger, by matching the shape of the heat exchanger (in particular, the cavity) to the shape of the container, the efficiency of the heating and/or cooling elements can be increased.

The BPC of the invention is designed to be utilized with a mixing device. In a first embodiment, a shaft of conventional (optionally disposable) agitator passes through an opening in the container, with the stirring element disposed therein. A motor is provided at the other end of the shaft to rotate the stirring element.

A second embodiment utilizes a magnetic agitator. A magnetic rod is placed inside the container and a magnetic field is generated by a magnetic drive device to rotate the rod. By locating a magnetic drive device external to the container, preferably outside the heat exchanger, the container need not have an opening and may be sealed, albeit with the rod and optional containment disk therein. The magnet rod may be disposed inside a containment disk.

Alternatively, the container and/or heat exchanger may include mixing devices mounted thereto. In a third embodiment, the container has a series of discontinuous baffles, such that when the baffles are alternatively inflated and deflated, the contents of the container can be stirred. Similarly, the container may have a series of fluid-filled sleeves, such that the mixing is performed when the sleeves are squeezed. In a final embodiment, the container includes, on the outside thereof, a series of hinged plates, and the cavity of the heat exchanger includes corresponding mechanical plates. When the mechanical plates in the cavity apply pressure to the hinged plates on the outside of the container, the bag is compressed and the contents thereof mixed.

BRIEF DESCRIPTION OF THE DRAWINGS

FIG. 3b is a side view of a containment disk of the invention.

FIG. 5a is an isometric view of a fourth embodiment of the invention.

FIG. 5b is an isometric view of a fifth embodiment of the invention.

FIG. 5c is an isometric view of a sixth embodiment of the invention.

DETAILED DESCRIPTION OF THE INVENTION

Figure 1:
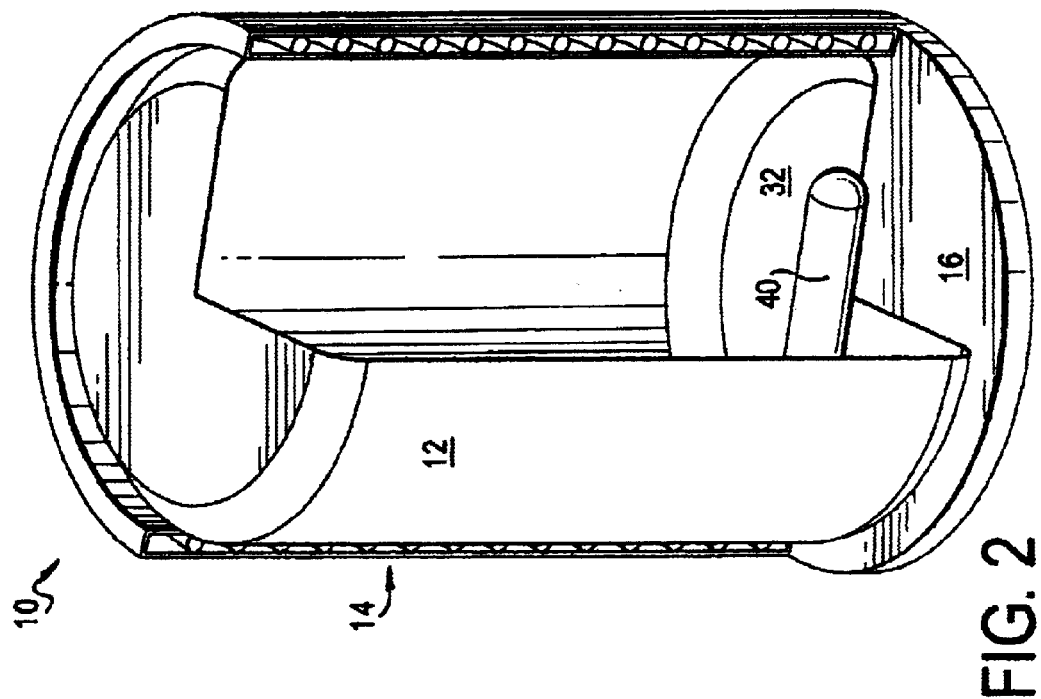
FIG. 1 is a partial is cut-away view of a first embodiment of the invention.

A bioprocess container (BPC) in accordance with the invention is shown in the various figures, each figure detailing an embodiment thereof. FIG. 1 shows a BPC 10, comprising a flexible container 12 in conjunction with a rigid, jacket-type heat exchanger 14. Specifically, heat exchanger 14 comprises a cavity 15, defined by a bottom 16, and side walls 18. For simplicity, container 12 is shown as being seated in heat exchanger 14, however, optionally, a small section may extend above side walls 18 heat exchanger 14. Although container 12 and heat exchanger 14 are shown in the shape of cylinders, any three-dimensional shape may be used. Preferably, however, the shape of cavity 15 of heat exchanger 14 is selected as to correspond to the size and shape of container 12 when filled. When the sizes and shapes correspond, the exterior surfaces of container 12 contact the interior surface of cavity 15 to increase efficiency of heat transfer therebetween. In any event, although the shape of each of container 12 and cavity 15 may be any three dimensional shape, e.g., rectangular prism, cubic, substantially spherical, pyramidal, and conical, a cylindrical shape, having either squared or rounded-off corners, is preferred.

Although the structure and size of container 12 is not particularly limited by the invention, preferably, container 12 is cylindrically shaped (approximately 36" diameter by 30" high) and made of polymeric materials, such as polyolefins, thermoplastic elastomers, polyamides, polyesters, polyimides, polysulphones, or barrier polymers (such as MX D 6 available from Mitsubishi Gas Chemical America, Inc. of New York, N.Y.; ethyl vinyl alcohol, polychlorotetrafluoroethylene, polyvinyl chloride). Most preferred however are polyolefins, thermoplastic elastomers and polyamides, alone or in combination. The polymeric materials may be processed in a multilayer laminate and/or film with a thickness from about 2 to about 12 mils, typically about 4 to about 8, and preferably from about 6 to about 8 mils.

Preferably, side walls 18 of heat exchanger 14 contain liquid-transfer media in spirally arranged tubes. Thus, when heating of the contents of container 12 is desired, the liquid-transfer media can be either heated or cooled to add or remove heat from container 12. During operation, the liquid transfer medium is pumped from an external location (where it is heated or cooled), through the tubes (transferring heat either to or from container 12), and back to the external location. In order to cool container 12, the liquid transfer medium is first cooled before it is pumped into the tubes.

In any event, the liquid-transfer media may be replaced by conventional heating or cooling coils, such as electric resistance or refrigerant-filled coils. Such heating and cooling coils may be provided independently or may both be incorporated into the same heat exchanger 14. For example, heat exchanger 14 preferably comprises a series of circular heat exchanger plates in side walls 18, providing a means for transferring heat out of the water by circulating a colder liquid through closed channels on the plate surface.

FIG. 1 also depicts a BPC mixing device comprising BPC 10. Specifically, the BPC mixing device comprises BPC 10 and an agitator 22. Agitator 22, in one embodiment, comprises a shaft 24, extending through an aperture 25 in a first end 26 of container 12 as to maintain sealing of container 12. It is considered within the scope of the invention for aperture 25 to be a one-way port, allowing introduction of agitator 22 without allowing exit of the contents of container 12. One extreme of shaft 24 terminates in a stirring element 28, inside container 12. Additionally, a motor 30 is connected to the section of shaft 24 external to container 12. Alternatively, however, shaft 24 may extend through a second end 32 of container 12 and optionally through bottom 16 of heat exchanger, such that motor 30 is disposed either integral with bottom 16 or below heat exchanger 14. Although FIG. 1, shows motor 30 disposed at the extreme opposite end from stirring element, as long as motor 30 is located outside container 12, any location is sufficient.

It must be noted that as used herein, the terms "stir", "mix" and "agitate" are considered equivalents and are interchangeable, as each simply means manipulating the contents of container 12 to, for example, to incorporate two substances (such as liquid into liquid or a solid into a liquid), or simply to disturb a single substance. Thus, no distinction should be inferred from the uses of these different terms.

Similarly, while stirring element 28 is depicted as a substantially flat, horizontally aligned device (with respect to the long axis of shaft 24), having multiple arms extending from a center, stirring element 28 need not be so limited. For example, stirring element 28 may be in the shape of a paddle extending vertically with respect to the long axis of shaft 24, or may have extensions extending in all three dimensions from shaft 24.

Figure 2:
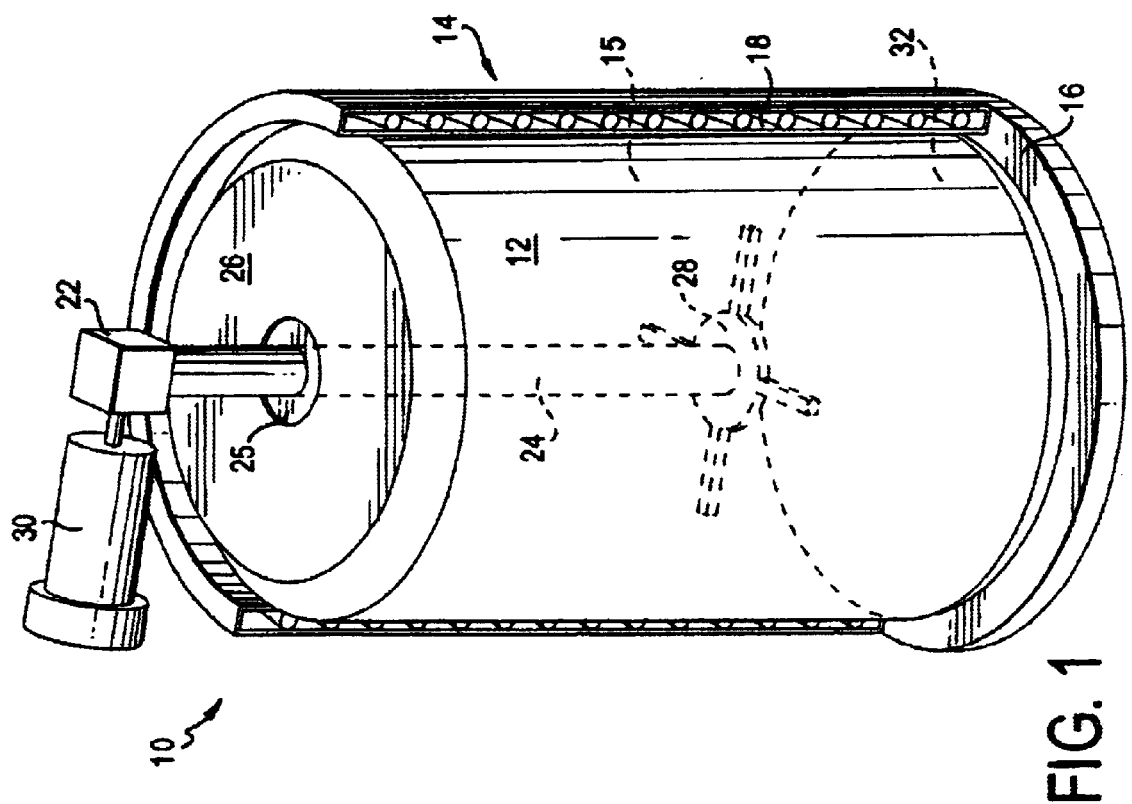
FIG. 2 is a partial cut-away view of a second embodiment of the invention.

FIG. 2 illustrates a second BPC mixing device embodiment in accordance with the invention. Specifically, the agitator in this embodiment comprises a magnetic rod 40 and a magnetic drive mechanism 42 (not shown). Magnetic drive mechanism 42 can be any device capable of generating a rotating magnetic field, such as a second magnetic rod attached to a motor, located either integral with heat exchanger 14, such as in bottom 16, or somewhere external thereto. In order to increase the efficiency of stirring created by the rotation of magnetic rod 40, the surface upon which magnetic rod 40 rotates, e.g., second end 32, may be provided with a non-stick or non-abrasive, low-friction coating, such as a polyolefinic material, preferably polytetrafluoroethylene. Although rod 40 is described as a magnetic rod, rod 40 may also be a magnetizable material, such as ferrous metals or ferrous metal-containing materials.

For example, in such an embodiment, 485 L of water can be cooled from 70.1° F. to 49.0° F. in 2.0 hours. The cooling liquid supply in the plates of heat exchanger 14 set-point is 38° F. with the closed system supply operating in a range from 38.5–46.9° F. Continuous motion of the contents of the disposable container 12, formed from a modified polyethylene, is generated by rod 40, having a tapered shape (e.g., diameter of 25 mm and 90 mm long), rotating at 650 rpm. By recording the water temperature at 8 locations, including 4 depths, 3 radial distances and 4 locating angles, the mixing of the contents of container 12 can be measured. The data shown in Table I indicates that when the invention is employed, even or uniform cooling can be achieved.

TABLE I

| Test Location No. | Location Angle (degrees) | Radial Distance (inches) | Depth (inches) | Temp. (° F.) |
|---|---|---|---|---|
| 1 | 0 | 18 | 24 | 60.5 |
| 2 | 90 | 18 | 18 | 60.4 |
| 3 | 180 | 18 | 12 | 60.6 |
| 4 | 180 | 9 | 6 | 60.7 |
| 5 | 180 | 9 | 24 | 60.8 |
| 6 | 180 | 0 | 6 | 61.3 |
| 7 | 180 | 0 | 24 | 61.2 |
| 8 | 270 | 9 | 18 | 61.3 |
| Mean | | | | 60.8 |
| Standard Deviation | | | | 0.366 |

In a second example, heat exchanger 14 heats the liquid in container 12, formed from a modified polyethylene, by circulating a liquid having a temperature hotter than the water in the in container 12. 446 L of water is heated from 41.9° F. to 77.6° F. in 1.3 hours, with the liquid in heat exchanger 14 having a set point of 95° F., and the closed system operating in a range from 77.1–96.2° F.

Figure 3A:
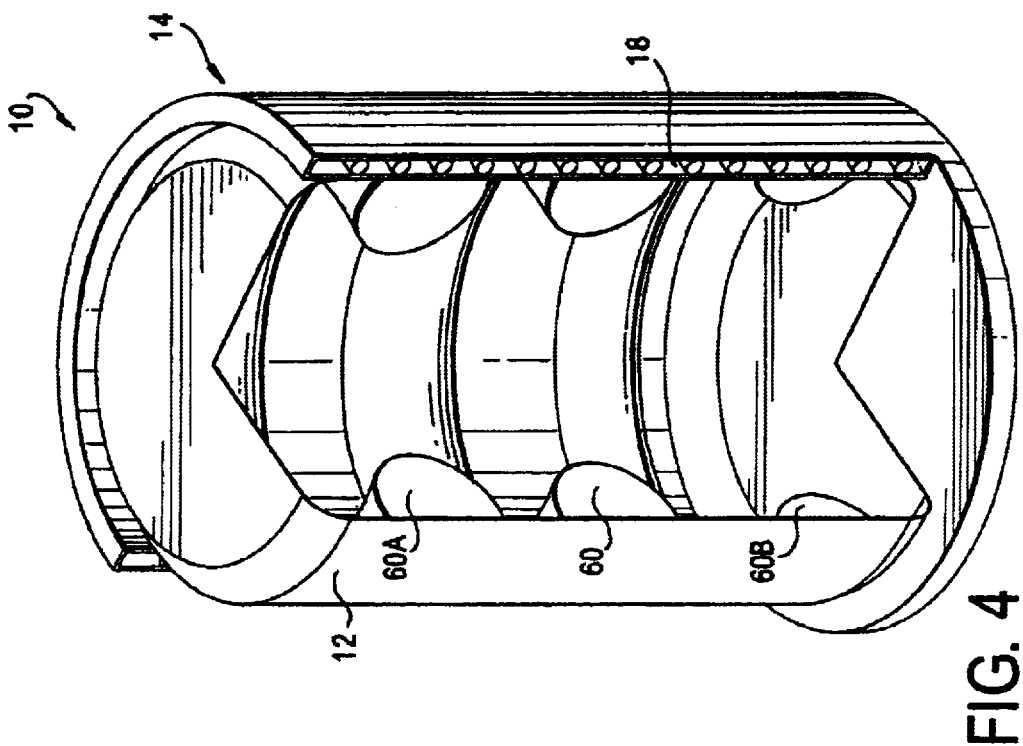
FIG. 3a is an exploded view of a rod containment device of the invention.

FIGS. 3a and 3b show a rod containment disk 100 of the invention. Conventional magnetic stirrers often become free from the magnetic field, and as a result, the mixing stops. Thus, the inventors have developed a containment disk, indicated at 100, into which magnetic rod 40 is placed. Due to the design of containment disk 100, rod 40 is prevented from exiting the magnetic field. In particular, containment disk 100 preferably has an upper ring 105 and a lower ring 108, which when assembled with bolts 110 and spacers 115, form the structure shown in FIG. 3b. The exploded view in FIG. 3a shows that bolts 110 pass through holes 112 in upper ring 105 and into threaded recesses 118 of lower ring 108. The length of bolts 110 and spacers 115 are preferably selected such that when constructed, the distance between upper ring 105 and lower ring 108 is large enough to allow rotation of rod 40 and permit substantially unobstructed fluid flow therein, while simultaneously preventing rod 40 from escaping containment disk 100. While containment disk 100 is shown in FIGS. 3a and 3b as being a separate device, it is preferable to integrate at lower ring 108 onto a plate 120. Typically plate 120 is adhered to or part of container 12 and serves as the surface upon which rod 40 rotates.

Typically, each of upper plate 105, lower plate 108, bolts 110 and spacers 115 are constructed from the same types of materials as container 12, preferably a polyolefin and more preferably low-density polyethylene. However, it is also considered within the scope of the invention to form any one of the components of containment disk of other materials, such as metal. In order to reduce friction, plate 120 is also preferably at least coated with a reduced-friction coating, such as polytetrafluoroethylene.

Preferably, each of the components of containment disk 100 is injection molded and once assembled, the components are ultrasonically welded together with rod 40 placed inside. Additionally, while upper ring 105 is shown as having a central aperture 125, in a preferred embodiment, this aperture 125 is not large enough for rod 40 to fit through without disassembling containment disk 100 and is merely present to increase fluid flow about rod 40.

Because conventional magnetic rods are often tapered at their ends, the space formed between upper ring 105 and lower ring 108 is preferably similarly tapered. Because the particular shape of the tapered surface can correspond to the shape of the particular shape of rod 40 to be enclosed therein, containment disk 100 can effectively allow rod 40 to rotate freely without risking it leaving the magnetic field.

Although it is preferable to position containment disk 100 at the bottom of container 12 with magnetic drive mechanism 42 located below container 12, it is also considered within the scope of the invention to mount containment disk 100 removed from the bottom of container 12. This may be accomplished, for example, with one or more feet supporting containment disk 100, or by attaching the outer circumferences of upper ring 105 and lower ring 108 to the inside wall of container 12 at the desired location. Finally, plate 120 may be eliminated and lower plate 108 be provided with an aperture when containment disk 100 is not positioned at the bottom of container 12 to allow for efficient fluid flow. In order to rotate rod 40, magnetic drive means 42 may comprise, instead of a rotating magnetic field, a pulsating magnetic field, alternating polarities to drive rod 40 inside containment disk 100.

Containment disk 100 may also be equipped with a baffle element 110 attached to upper ring 105 (FIG. 3*b*). Preferably, baffle element 110 is included to hinder or otherwise prevent the contents of container 12 from forming a vortex during agitation. In conventional mixing devices using a magnetic rod, if any air is trapped inside the container, rotation of the magnetic rod causes the liquid to form a vortex, necessarily drawing air into the liquid. By including baffle element 110, the rotation of the liquid can be disrupted enough to limit any vortex formation, while increasing mixing efficiency. Preferably, baffle element 110 is similar in structure to upper ring 105, but may alternatively be of any shape or size capable of hindering the vortex-causing forces, for example, a rectangular prism, thin vertically-extending flange or pyramid. Additionally, a second set of spacers 130 maintain a space between baffle element I 10 and upper ring 105. Although spacers 130 are show as being substantially similar in size to spacers 115, the particular dimensions of spacers 130 are preferably selected as to position baffle element 110 in the location where the vortex-causing forces are greatest.

In an additional set of embodiments, the contents of container 12 are stirred by physically changing the shape and/or dimensions of container 12. By applying pressure to a particular area or location of container 12, the contents are displaced and moved to another location inside container 12. Thus, a shape manipulating means is utilized to stir the contents of container 12.

Figure 4:
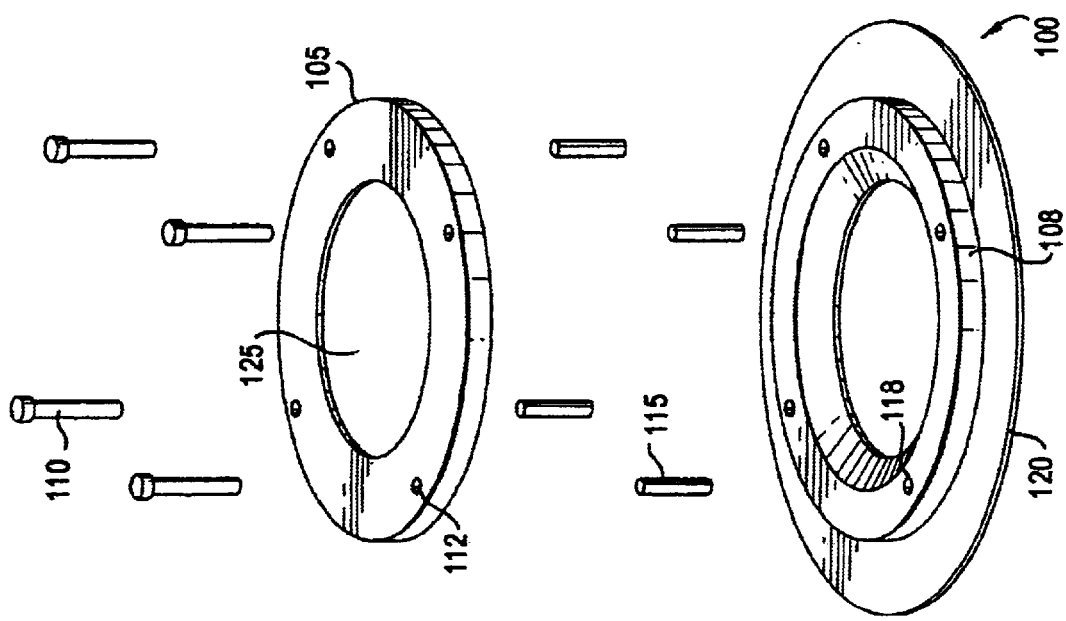
FIG. 4 is a partial cut-away view of a third embodiment of the invention.

In a third embodiment, depicted in FIG. 4, container 12 comprises at least one bladder 60, capable of being filled with a fluid disposed about the periphery of container 12. In order to selectively inflate and/or deflate bladders 60, an inflating apparatus 62 (not shown), such as an air or water pump is provided. Specifically, by forming an inflated bladder 60*a*, and a deflated bladder 60*b*, container 12 can be manipulated to create forces therein to mix the contents. While bladders 60 are preferably formed integral with the structure of container 12, it is also considered within the scope of the invention to form bladders 60 in side walls 18 of heat exchanger 14 or as a separate inflatable/deflateable element between side walls 18 and container 12 (in which case bladders 60 may be affixed to side walls 18 and/or container 12 in a removable or permanent fashion). Bladders 60 may also be in fluid communication with conduits carrying the liquid-transfer media, such that by simply altering the volume or pressure of the liquid-transfer media, the shape of container 12 can be changed. Additionally, baffles 60 may be a single unit, or alternatively, multiple discontinuous units.

In a third example, liquid syrup was mixed with water in a flexible container and single continuous bladder supported by a rigid outer structure. The flexible container was cylindrically shaped, having a diameter of 8 inches, and a circumferential bladder (4 inches in diameter and 440 cubic inches in volume) located at one end. Both the container and bladder were formed from a plastic film, processed into a multilayer laminate with a thickness between about 2 and about 12 mils. A cylindrical outer structure, having an 11 inch diameter was also provided. One milliliter of liquid syrup was introduced at the bottom of 1.7 gallons of water. After 29 cycles (each cycle including inflating the bladder completely with air and subsequently deflating the bladder) over 2 minutes, approximately 90% of the syrup had become mixed into the water. This mixing percentage can be determined by any sufficient means, for example, by measuring optical color change or opacity of the water.

Furthermore, bladders 60 may be replaced by other devices designed to manipulate the shape of container 12 as to agitate the contents disposed therein. For example, FIG. 5*a* shows container 12, wherein static fluid-filled sleeves 70 are attached to the exterior. Thus, in order to change the shape of container 12, one or more sleeves 70 are squeezed by, for example, a clam-shell device, indicated at 71, which may be motorized or actuated manually. In order to perform the agitating, clam-shell devices 71 simply clamp down on sleeves 70 to force the contents of sleeves 70 into the main body of the container. When more than one sleeve 70 is provided, the sleeves 70 may be squeezed simultaneously or independently.

One or more arms 80 may be attached to container 12, as shown in FIG. 5*b*, such that when arms 80 are pushed, container 12 is deformed and fluid is forced from the area in proximity to arms 80. Preferably, a stationary baffle 81 is provided near arms 80, such that before entering the main section of container 12, the fluid must first pass stationary baffle 81. Additionally, arms 80 may be pulled to deform container 12 by stretching. Preferably, when arms 80 are utilized container 12 resembles a rectangular prism or a cube, with arms 80 positioned at the edges thereof. Most preferably, arms 80 are disposed at the edges, most preferably at each of the corners of container 12.

Finally, container 12 may be provided with a system comprising at least one hinged plate 90 (FIG. 5*c*), while heat exchanger 14 includes at least one mechanical plate 95, corresponding to the location and number of the hinged plates, such that mechanical plates may be activated to create a pulsation in container 12. Preferably, mechanical plates 95 in heat exchanger 14 correspond in number and position to hinged plates 90 in container 12, such that each mechanical plate 95 impinges upon a separate hinged plate 90. Thus, the manipulation of hinged plates 90 functions to massage container 12 to agitate the contents therein.

Although the present invention has been described in terms of specific embodiments, it will be apparent to one skilled in the art that various modifications may be made according to those embodiments without departing from the scope of the applied claims and their equivalents. Accordingly, the present invention should not be construed to be limited to the specific embodiments disclosed herein.

We claim:

1. A BPC mixing device comprising:
    a flexible container having a size and a shape when at least partially filled, and
    a rigid heat exchanger, comprising liquid-transfer media, having a heat exchanging cavity said container disposed at least partially inside said cavity and in contact with said heat exchanger, said heat exchanging cavity having a portion which corresponds essentially to a portion of the shape of said container; and
    at least one manipulating element selected from the group consisting of:
    at least one bladder integral with or adjacent to the structure of said container and at least one inflating apparatus, in fluid communication with said at least one bladder; and
    a plurality of fluid-containing sleeves protruding from the interior of said container and a means for squeezing said plurality of fluid-containing sleeves.

2. The BPC of claim 1, wherein said container is in the shape of a cylinder, having a rounded surface, a closed first end and a closed second end, said second end disposed inside said cavity.

3. The BPC mixing device of claim 1, wherein the manipulating device is at least one bladder integral with or adjacent to the structure of said container and at least one inflating apparatus, in fluid communication with said bladder.

4. A method for mixing comprising:
    providing a bioprocess container (BPC), said BPC comprising:
        a flexible container having a size and shape when at least partially filled, and
        a rigid heat exchanger, having liquid-transfer media and a heat exchanging cavity, said container disposed at least partially inside said cavity and in contact with said heat exchanger, said cavity having a portion corresponding essentially to the shape of said container and
        at least one manipulating element selected from the group consisting of:
            at least one bladder integral with or adjacent to the structure of said container and at least one inflating apparatus, in fluid communication with said at least one bladder; and
            a plurality of fluid-containing sleeves protruding from the interior of said container and a means for squeezing said plurality of fluid-containing sleeves; and
    agitating the contents of the container.

5. The method of claim 4, wherein said agitating is selected from the group consisting of:
    manipulating the shape of the container, by selectively inflating and deflating said at least one bladder.

6. The method of claim 5, wherein said manipulating is selected from the group consisting of
    selectively inflating and/or deflating at least one bladder integral with the structure of said container; and
    selectively squeezing a plurality of fluid-containing sleeves protruding from the interior.

* * * * *